US011915127B2

(12) United States Patent
Saripalli et al.

(10) Patent No.: US 11,915,127 B2
(45) Date of Patent: Feb. 27, 2024

(54) PREDICTION OF HEALTHCARE OUTCOMES AND RECOMMENDATION OF INTERVENTIONS USING DEEP LEARNING

(71) Applicant: Edifecs, Inc., Bellevue, WA (US)

(72) Inventors: Kanaka Prasad Saripalli, Danville, CA (US); Frank Lucas Wolcott, Seattle, WA (US); Paul Raymond Dausman, Franklin, WI (US); Shailly Saxena, Seattle, WA (US); William Lee Clements, Redmond, WA (US)

(73) Assignee: Edifecs, Inc., Bellevue, WA (US)

( * ) Notice: Subject to any disclaimer, the term of this patent is extended or adjusted under 35 U.S.C. 154(b) by 827 days.

(21) Appl. No.: 16/963,094

(22) PCT Filed: Aug. 3, 2019

(86) PCT No.: PCT/US2019/045023
§ 371 (c)(1),
(2) Date: Jul. 17, 2020

(87) PCT Pub. No.: WO2020/028890
PCT Pub. Date: Feb. 6, 2020

(65) Prior Publication Data
US 2020/0356846 A1 Nov. 12, 2020

Related U.S. Application Data

(60) Provisional application No. 62/714,483, filed on Aug. 3, 2018.

(51) Int. Cl.
*G06N 3/063* (2023.01)
*G16H 10/60* (2018.01)
(Continued)

(52) U.S. Cl.
CPC ............. *G06N 3/063* (2013.01); *G06N 3/045* (2023.01); *G16H 10/60* (2018.01); *G16H 50/20* (2018.01)

(58) Field of Classification Search
None
See application file for complete search history.

(56) References Cited

U.S. PATENT DOCUMENTS

| 2010/0277173 A1 | 11/2010 | Landschuetz et al. |
| 2017/0265754 A1 | 9/2017 | Sharma et al. |

FOREIGN PATENT DOCUMENTS

WO 2017122785 A1 7/2017

OTHER PUBLICATIONS

Tang, et al., Multimodal Emotion Recognition Using Deep Neural Networks, ICONIP 2017, Part IV, LNCS 10637, 2017, pp. 811-819 (Year: 2017).*

(Continued)

*Primary Examiner* — Wilbert L Starks
(74) *Attorney, Agent, or Firm* — Nixon Peabody LLP

(57) ABSTRACT

A system includes first, second and third input data sets. The first input data set includes demographic information characterizing a patient. The second and third input data sets characterize a healthcare treatment history of the patient. A neural network includes first, second and third neural subnetworks. The first neural subnetwork is configured to process the first input data set to produce a first output data set. The second neural subnetwork is configured to process the second input data set to produce a second output data set. The third neural subnetwork is configured to process the third input data set to produce a third output data set. An autoencoder layer has an input layer comprising the first, (Continued)

second and third output data sets and is configured to process the first, second and third output data sets to produce a secondary output data set.

12 Claims, 5 Drawing Sheets

(51) Int. Cl.
*G16H 50/20* (2018.01)
*G06N 3/045* (2023.01)

(56) References Cited

OTHER PUBLICATIONS

International Search Report and Written Opinion for Application No. PCT/US2019/045023, dated Oct. 22, 2019, 9 pages.
Nezhad, M. et al., "A Predictive Approach Using Deep Feature Learning for Electronic Medial Records: A Comparative Study," [online publication] Jan. 6, 2018 [retrieved online: Sep. 29, 2019] Retrieved from the Internet: <URL: https://arxiv.org/pdf/1801.02961.pdf>, 25 pages.

* cited by examiner

PREDICTION OF HEALTHCARE OUTCOMES AND RECOMMENDATION OF INTERVENTIONS USING DEEP LEARNING

PRIORITY CLAIM

The present application is a 35 U.S.C. § 371 national phase of Application No. PCT/US2019/045023 filed Aug. 3, 2019; which claims priority from U.S. Provisional Application No. 62/714,483 filed Aug. 3, 2018. The above-referenced applications are hereby incorporated by reference in their entireties as if fully set forth herein.

BACKGROUND

In the past, traditional business intelligence (BI) and statistical methods have been used on electronic health records (EHR) (Clinical data) and claims data separately to make predictions about diseases. Recently, machine learning has been used on data sets for similar clinical predictions. Separately, machine learning (ML) has also been used on claims data for healthcare related predictions. Deep learning has been used recently to develop methods such as deep patient focused on the use of EHR data alone. There have been no attempts to apply either machine learning or deep learning to aggregated clinical and administrative data sets, including lab and pharmacy data, for better healthcare outcomes.

BRIEF DESCRIPTION OF THE DRAWING FIGURES

Preferred and alternative examples of the present invention are described in detail below with reference to the following drawing figures.

DETAILED DESCRIPTION

Figure 1:
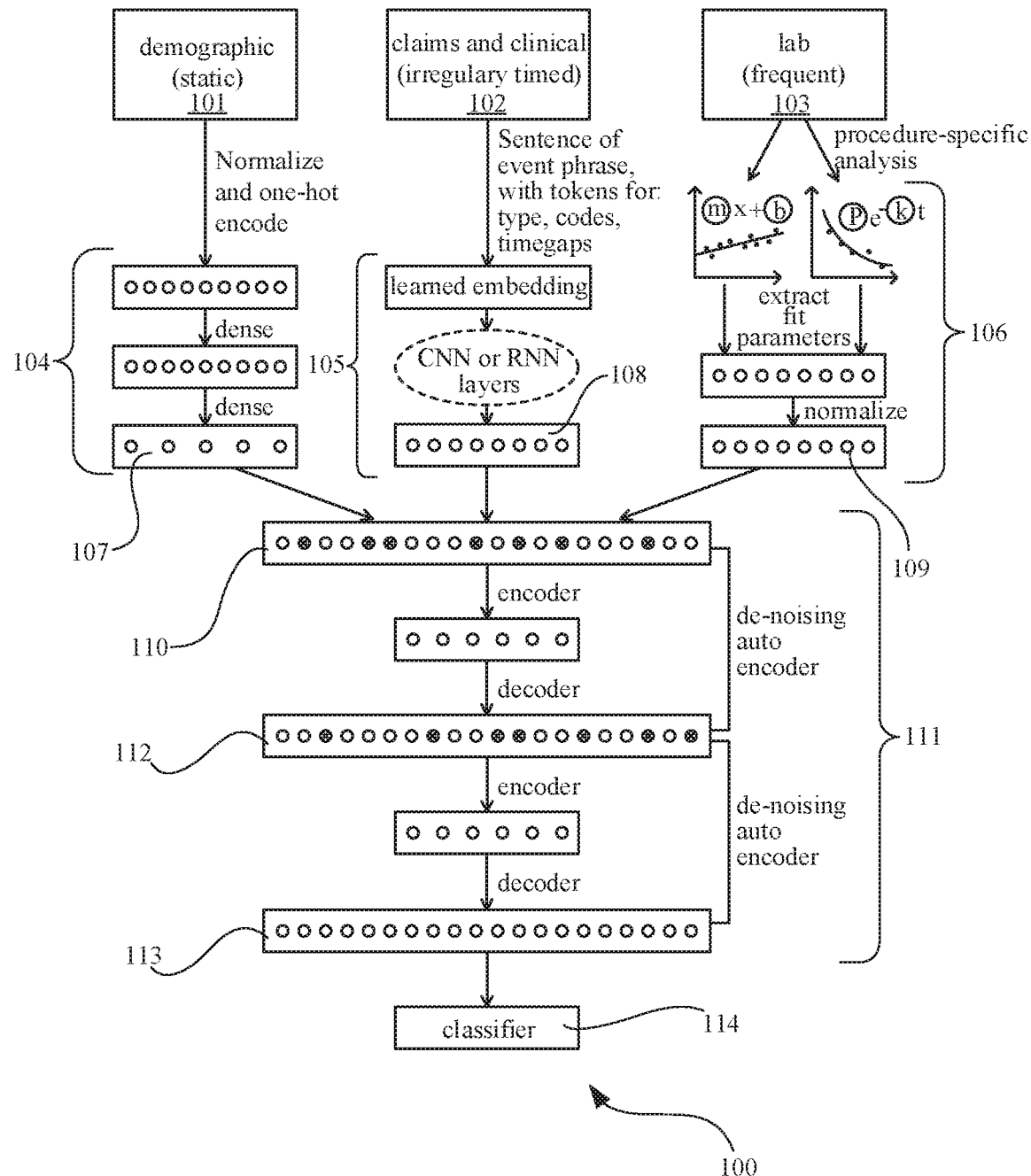
FIG. 1 is a schematic view of a deep-learning neural network according to an embodiment of the invention.

This patent application is intended to describe one or more embodiments of the present invention. It is to be understood that the use of absolute terms, such as "must," "will," and the like, as well as specific quantities, is to be construed as being applicable to one or more of such embodiments, but not necessarily to all such embodiments. As such, embodiments of the invention may omit, or include a modification of, one or more features or functionalities described in the context of such absolute terms.

Embodiments of the invention may be described in the general context of computer-executable instructions, such as program modules, being executed by a processing device having specialized functionality and/or by computer-readable media on which such instructions or modules can be stored. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

Embodiments of the invention may include or be implemented in a variety of computer readable media. Computer readable media can be any available media that can be accessed by a computer and includes both volatile and nonvolatile media, removable and non-removable media. By way of example, and not limitation, computer readable media may comprise computer storage media and communication media. Computer storage media include volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by a computer. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media. In some embodiments, portions of the described functionality may be implemented using storage devices, network devices, or special-purpose computer systems, in addition to or instead of being implemented using general-purpose computer systems. The term "computing device," as used herein, refers to at least all these types of devices, and is not limited to these types of devices and can be used to implement or otherwise perform practical applications.

According to one or more embodiments, the combination of software or computer-executable instructions with a computer-readable medium results in the creation of a machine or apparatus. Similarly, the execution of software or computer-executable instructions by a processing device results in the creation of a machine or apparatus, which may be distinguishable from the processing device, itself, according to an embodiment.

Correspondingly, it is to be understood that a computer-readable medium is transformed by storing software or computer-executable instructions thereon. Likewise, a processing device is transformed in the course of executing software or computer-executable instructions. Additionally, it is to be understood that a first set of data input to a processing device during, or otherwise in association with, the execution of software or computer-executable instructions by the processing device is transformed into a second set of data as a consequence of such execution. This second data set may subsequently be stored, displayed, or otherwise communicated. Such transformation, alluded to in each of the above examples, may be a consequence of, or otherwise involve, the physical alteration of portions of a computer-readable medium. Such transformation, alluded to in each of the above examples, may also be a consequence of, or otherwise involve, the physical alteration of, for example, the states of registers and/or counters associated with a processing device during execution of software or computer-executable instructions by the processing device.

As used herein, a process that is performed "automatically" may mean that the process is performed as a result of machine-executed instructions and does not, other than the establishment of user preferences, require manual effort.

Electronic health records hold great promise for enabling analytics in support of predicting healthcare outcomes with machine learning. Potential and accuracy of such analytics strongly depends on the features or attributes contained in the data sets.

One or more embodiments of the present invention are based on the premise that (1) in addition to EHR, other healthcare related data sets—especially the administrative (i.e., claims) data maintained by the payers can significantly enrich the machine learning outcomes; and (2) integrating EHR, pharmacy, lab data, administrative and/or payer claims data, socioeconomic and population-related data and patient-generated data can further enrich the same. This enrichment can be derived in two ways—enabling a much broader set of use cases or questions of prediction, and enhancing the accuracies of such predictions. A deep claim according to an embodiment is the healthcare industry's first attempt at the use of deep learning, in this context, using such aggregated data sources. Aggregation of healthcare data sets leads to a much more information-rich base pattern in the data, which can lead to enabling a wider set of predictions, better feature engineering and better accuracies of prediction.

Deep feature learning has not been applied so far to generate general-purpose representations of not only patients but an overarching number of healthcare objects including patients, procedures, claims, providers, payers, etc. using EHR and other lab, pharmacy and administrative aggregated data. Modeling healthcare processes as encounters among such multiple objects of which the patient is only one key object leads to further development of deep learning applications to healthcare data sets.

In an embodiment, a Payer-Provider-Pharma-Patient-Lab master data structure is derived from a combination of standard healthcare data formats such as the UB-04 Form for inpatient claims as well as the HIPAA 1500 claim format for professional claims. These base data sets are combined with prescription claims, lab claims, member demographics, enrollment and provider attributes to create one comprehensive claims data repository from which to learn. This repository is further enriched by the loading of corresponding reference data sets that further explain the meaning and significance of the code sets found within the underlying claims data.

An embodiment, which may be referred to as Deep Claim, uses, for example, Apache Spark™ to engineer deep learning features from this master data structure, in a way that scales for Big Data. An embodiment integrates temporally dependent attributes (e.g., EHR and claim data) with static attributes (e.g., demographics) in a novel way. The temporal attributes are combined as phrases of tokens, separated by time duration keywords, into sentences using natural language processing methods (e.g., tokenization, stopword/rareword processing). These temporal attributes are fed into a deep neural network that includes a learned embedding layer, locally connected layers (convolutional, recurrent), and dense layers. The static attributes are preprocessed and fed into dense layers, joined with the temporal architecture, and then connected to stacked de-noising autoencoders. The result is a generic data representation that incorporates diverse data sources, and is robust to missing or corrupted data.

Optionally advantageous features of one or more embodiments of this invention are: (i) aggregation of healthcare data from diverse sources, especially the payer and provider for better deep learning; (ii) automated feature selection via deep learning; (iii) enablement of a much wider range of analytics predictions and use cases than is possible using EHR alone; and (iv) better prediction accuracies, which is the hallmark of deep learning.

An embodiment leverages deep learning methodology (e.g., natural language processing, convolutional and recurrent neural nets, embeddings), combined with the most-recent state-of-the-art developments (stacked de-noising autoencoders, attention) in a novel architecture. The resulting data representation is use-case agnostic and can be trained, applied, and transferred among use cases.

Machine learning (ML) and artificial intelligence (AI) based approaches have the potential to significantly help the analytic and decision-making processes involved in the clinical, caregiving, pharmaceutical and administrative functions of the healthcare industry. Data is at the heart of this technological promise—outcomes from machine learning when based on the best available, integrated data sources can be critical to the successful adoption of ML and AI in healthcare. In this context, it is useful to model the healthcare ecosystem as a world of objects (animate, inanimate and abstract; for example, patients, doctors, nurses and diseases, procedures, facilities, devices, claims, payments, etc.) and encounters among such objects. Data sets collected as feature or attribute values about all such objects and models of their interactions are the keys to a successful adoption of ML for deriving analytic value.

Thus, to realize the true potential of ML and AI it is optionally advantageous to develop methods and tools that can facilitate (i) the aggregation of information-rich data from all objects and their encounters from all available sources; (ii) construction of an elaborate set of use cases and their conversion to suitable, rigorous ML questions and (ii) engineering of features and algorithms that can answer the ML analytic questions efficiently. An embodiment includes the first such comprehensive methodology that addresses all of the said criteria satisfactorily.

In the past, traditional business intelligence (BI) and statistical methods have been used on EHR (Clinical data) and claims data separately to make predictions about diseases. Recently, machine learning has been used on EHR data sets for similar clinical predictions. Separately, ML has also been used on claims data for healthcare related predictions. Deep learning has been used recently to develop methods focused on the use of EHR data alone. There were no attempts to apply either machine learning or deep learning to aggregated clinical and administrative data sets, including lab and pharmacy data as proposed here for better healthcare outcomes. Aggregation of healthcare data sets in this manner leads to a much more information-rich base pattern in the data which would lead to enabling a wider set of predictions, better feature engineering and better accuracies of prediction.

As above alluded to, deep feature learning has not been applied so far to generate general-purpose representations of patients or an overarching number of healthcare objects including procedures, claims, providers, payers, etc. using EHR and other lab, pharmacy and administrative aggregated data. Modeling healthcare processes as encounters among such multiple objects of which the patient is only one key object leads to further development of deep learning applications to healthcare data sets.

An embodiment sources its data from a data structure that incorporates standard payer claim transaction data sets combined with related reference data from all over the organization. The current industry standard is to combine those standardized claim data sets with a limited set of tables and attributes that are largely focused on the claims payment process. An embodiment widens the scope of the data sets employed to make critical financial and clinical predictions about the operations and health of the plan and its members. The primary areas of this expansion, segmenting and integrating the traditional Claims and EHR datasets, are as follows:

Standardized Measures: Health plans are incentivized to maximize their performance on Center for Medicaid and Medicaid (CMS) measurement programs such as Medicare Advantage Five Star, Health Insurance Marketplace Quality Rating System (QRS) and many State based Medicaid Alternative Payment Model programs. An embodiment employs the results of these standardized measurements as a valuable source of predictive learning.

Social Determinates of Health (SDOH): Expanding the information known about a member beyond simple demographic, payment or clinical related data sets to attributes that encompass advanced demographics such as social support, income level, geographical location, mental health and employment greatly enhances the abilities of the learning engine.

Enhanced Pharmacy Data: Pharmacy data and its analysis are commonly a second-class citizen with health plans due to many of the pharmacy functions and responsibilities being contracted out to Pharmacy Benefit Management organizations. An embodiment not only includes the usual standardized pharmacy claim data sets but uses an expanded set of reference data sets that enrich the data set beyond just recording of claim events to understanding the adherence of the member to their drugs and how the prescribing process drives optionally advantageous relationships and future health status of the member.

Value Based Care Contracting and Population Management: As the concepts of Value Based Care and Alternative Payment Models become more entrenched in the industry, the terms of the contracts that drive these new relationships between payers and providers will have a great impact on the predictions of an embodiment about the direction of a member's healthcare. Aggressive management of members' health can alter how a member would typically behave, making predictions based solely on past events highly inaccurate.

Claim Metadata: Often the data about the claims data itself and its lifecycle can be highly valuable to the process of making predictions about future claims payment issues as well as extended into the clinical side of decision making as well. An embodiment consumes various data sets that inform the prediction engines about who is asking for payment, what is actually paid, what isn't paid and why.

An embodiment's (Deep Claim) architecture includes a proper integration of all of the above datasets that creates a distinct and novel advantage for health plans that employ its algorithms to make predictions and decisions about member healthcare and payment processes. Such integration, coupled with deep learning's ability to search through large data spaces and identify optimal combinations of features to answer unique and novel learning questions leads to better and more accurate outcomes.

Below herein, different components of an embodiment and how they contribute to its novel architecture are described. An embodiment combines three categories of sophisticated neural networks as subnetworks to utilize the unique structure of input data conquering the challenges related to temporal and spatial nature of the data. These are deep networks that utilize a huge number of varieties of neurons and complex architectures that may include a feed-forward multilayer network and the ability of automatic feature extraction.

One or more of these subnetworks according to an embodiment may employ a convolutional neural network (CNN). CNNs are deep artificial neural networks that are inspired by the visual cortex of animals. Thus, they are inherently effective in image recognition and classification, and they are widely adapted in language processing tasks as well.

CNN's success with natural languages and their capability of finding latent patterns make them a strong candidate for an architecture according to an embodiment. Coded healthcare information might contain otherwise hidden patterns or grammar that could provide breakthroughs in various complex prediction problems like unplanned hospital readmissions, palliative care, heart failure, etc.

A convolutional network according to an embodiment includes a convolution layer that comprises multiple filters of variable sizes, the weights of which are learned during a training process. A convolution is essentially a matrix operation on the input data performed by sliding a filter on the input data to extract features maps. Every filter is slid such that the entire input is covered (how a filter slides can be controlled by defining strides).

In an embodiment, there are three types of layers in a CNN—an input layer, feature-extraction layers and classification layers. Input layers take multi-dimensional text embedding as input. The classification layers comprise a dense layer and send the learned features forward to produce classification scores. In an embodiment, features from previous layers are taken and the results are sent to stacked denoising autoencoders for further processing.

An embodiment's feature-extraction layers consist of a convolutional layer (a collection of filters) that is followed by an activation layer to introduce non-linearity and feature mapping. This enables the network to learn hidden local patterns in data that are predictive in nature. A pooling layer then follows that is used to downsample the filter map—an embodiment uses max-pooling that outputs the maximum value from an activation map. An embodiment also adds dropout layers that prevent overfitting by setting a random set of activation maps to 0.

Every filter in an embodiment's CNN learns a predictive local pattern in data and that are co-occurrences of diseases (also known as comorbidity), disease progression, patterns of disease/treatment, and patterns of collocating treatments.

Time is a crucial factor in healthcare data, and in order to make successful predictions feasible, it is optionally advantageous to model time-dependent variables present in this data. Certain types of neural networks are inherently capable of modeling sequences that are time-dependent—recurrent neural networks being one of them. Such models have 'memory' that enables them to remember sequences of inputs. An embodiment effectively utilizes such networks for its irregularly-timed claims and clinical data.

Artificial neural networks whose layers are attached to each other in a manner such that the previous layers feed the next are known as feed-forward networks. Such networks do not contain any cycles. One or more of the subnetworks according to an embodiment may employ a recurrent neural network (RNN). RNNs contain cycles and understand the history of data. With regard to healthcare data, recent events are, in some cases, of more importance as compared to older events, while in other cases, older events are as useful as new ones. RNNs have unlimited memory and can learn to grasp long—as well as short-term dependencies that are relevant to predict the future outcomes.

RNNs, in essence, do not capture long-term dependencies so well because of the vanishing-gradient problem. An embodiment implements long short-term memory (LSTM) units as the building blocks of RNN layers. They perform exceedingly well and can store both long- and short-term values. A basic structure of LSTM consists of a memory cell, an input gate, an output gate and a forget gate. The memory cell stores information regarding what is useful to remember, the forget gate, as the name suggests, removes what is not important. An embodiment implements a bidirectional LSTM that trains two instead of one LSTMs on an input sequence: one in the forward direction and one in the backward direction, which further enhance performance.

By utilizing LSTMs, an embodiment can also predict outcomes for patients about which it has not seen a lot of history by learning sequences from other similar patients since LSTMs can learn from a varying number of previous time steps and do not require a pre-decided n number of visits for all patients in order to make predictions.

One of the features of an embodiment is its use-case agnostic property, which allows utilization of the same architecture for different problems. This is achieved by applying autoencoders, which are unique neural network architectures capable of learning input data representations in an unsupervised manner. These representations are the most efficient forms of the input data and reduce the dimensionality of data considerably.

Autoencoders, in their simplest forms, are feedforward networks with an input layer, hidden layers and an output layer. Dimensions of the output layer are the same as that of the input layer so that the network can learn its own representation of the input data. Learning in autoencoders is done by first encoding the data by passing it through hidden layers and then decoding it to learn concepts of input data.

Another feature of an embodiment is its ability to handle missing and corrupted data related to the healthcare industry. This problem may be solved by stacking two de-noising autoencoders (called Stacked Denoising Autoencoders or SDA) with a 5% salt and pepper noise. By introducing noise in the network, we are able to learn more robust representations of the incoming data, and the overall network becomes less prone to side-effects of noise—most optionally advantageous being unreliable predictions.

In the architecture of an embodiment, three sources of data combine together to form an input for the SDA. The first input is the static demographic information. The second input is the irregularly timed claims and clinical data. The third input is the frequent lab data. At the junction where SDAs begin their work in the architecture, an embodiment brings together these different forms of data and introduces random noise. SDAs then learn robust representations and an embodiment eventually learns to make successful predictions.

As alluded to above herein, a deep learning neural network 100 according to an embodiment consists of three types of inputs that are fed into separate subnetworks, then joined in a single layer that is then connected to stacked de-noising autoencoders as illustrated in, for example, FIG. 1.

The three types of inputs coming from the master data structure and distinguished by their temporal characteristics are described below.

Static demographic data input 101 includes data that is treated as static, as it is unlikely to change significantly, if at all, over the period of interest. Such data may include, for example, age, gender, race/ethnicity, and geographic data.

Irregularly or randomly timed claims and clinical data input 102 (i.e., administrations of health care not of a predetermined frequency to the patient) includes medical claims—professional, outpatient, and inpatient—as well as prescription claims, infrequent lab tests, and other EHR data.

Lab results input 103 includes numerical measurements characterizing the health status of the patient. This may include, for example, frequently taken patient measurements via a pre-planned corresponding procedure, such as vital signs or blood levels, the levels of which can vary over time and which can be converted, by an embodiment or otherwise, into a time-based function and/or series and analyzed in this form.

Additionally, the following types of data can also be fed to the stack: (i) patient-generated healthcare data (PGHD) including social networks data, (ii) pharmaceutical data and (iii) data on the social determinants of health collected from other sources such as the census, employment, etc.

In an embodiment, and as illustrated in FIG. 1, neural network 100 includes a first neural subnetwork 104, a second neural subnetwork 105, and a third neural subnetwork 106. Provided below is detail of how each of these types of inputs are treated by the subnetwork architectures, along with a description of how they are merged and further processed.

First neural subnetwork 104 processes data input 101 to produce a first output data set that can be output by a first primary output layer 107. Numeric data such as age may be scaled to have a mean of zero and variance of one. Categorical variables are one-hot encoded, with a possible binning step to reduce the number of classes (e.g., binning states into NE, SE, SW, NW classes). These inputs are provided to two hidden dense layers as illustrated in FIG. 1.

Second neural subnetwork 105 processes data input 102 to produce a second output data set that can be output by a second primary output layer 108. Each patient or member's data is processed into a sentence of codes and keyword tokens in a manner similar to that described in P. Nguyen, T. Tran, N. Wickramasinghe, and S. Venkatesh, "Deepr: A Convolutional Net for Medical Records," *ArXiv*160707519 *Cs Stat*, July 2016 ("Deepr paper"), which is hereby incorporated by reference as if fully set forth herein. In the Deepr paper, the authors use procedure and diagnosis codes from inpatient claims data only. An implementation according to an embodiment extends to include outpatient, professional and prescription data, as well as infrequent lab results, by including indicator keywords (e.g., "IN", "OUT", "PRF"). An embodiment includes procedure and diagnosis codes, but also allows incorporation of tokens derived from free-text clinical notes in a manner similar to that described in R. Miotto, L. Li, B. A. Kidd, and J. T. Dudley, "Deep Patient: An Unsupervised Representation to Predict the Future of Patients from the Electronic Health Records," *Sci. Rep.*, vol. 6, p. 26094, May 2016 ("Deep Patient paper"), which is hereby incorporated by reference as if fully set forth herein.

Infrequent lab results are binned and tokenized in a manner similar to that described in A. Rajkomar et al., "Scalable and accurate deep learning with electronic health records," *Npj Digit. Med.*, vol. 1, no. 1, December 2018 ("Scalable paper"), which is hereby incorporated by reference as if fully set forth herein. Tokens that occur infrequently in the dataset are replaced by "RAREWORD".

Individual items in a member's history are sorted by date of service, and the time duration between events is calculated, then binned into appropriately-spaced classes indicated by keywords (e.g., "10-30D" to signify a time gap of ten to thirty days).

Below is an example of part of an input member sentence:
  IN 2769 3051 V551 10-30D OUT 6826 RAREWORD 1-3M IN 1623 99591 2769 RAREWORD RAREWORD 3051 4280 5781 V551 9671 6826 5990 10-30D . . . .

Interpreting this sentence, this member had an inpatient event that was submitted with the codes 2769, 3051, and V551. Then a period of 10-30 days elapsed and there was an outpatient visit that included code 6826 and a rare code. After one to three months, there was another inpatient event with twelve codes submitted.

To further process these claim sentences, an embodiment post-pads the sentence so they all have fixed length num_tokens. They are fed into an embedding layer of fixed dimension emb_dim, randomly initialized, which is learned during training. The result for each training sample is a numpy array with shape (num_tokens, emb_dim). The embedding dimension is a hyperparameter that requires tuning; according to an embodiment, 50 offers the best performance.

In varying embodiments, there are two options for subnetwork architecture, and the one to use depends on the data available and performance considerations. One is based on CNNs, and the other on RNNs. Both are broadly described below herein.

Figure 2:
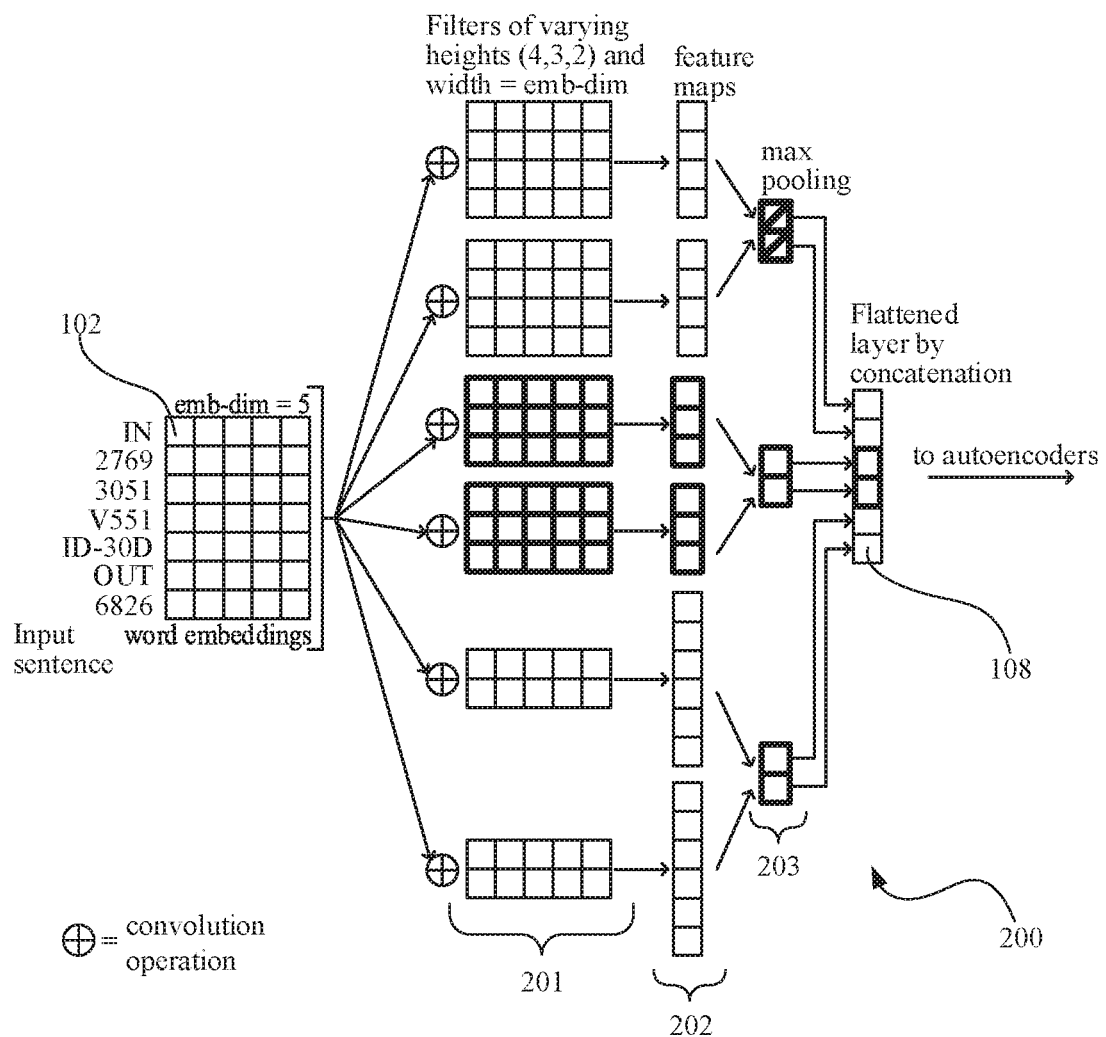
FIG. 2 is a schematic view of a convolutional neural network according to an embodiment of the invention.

Convolutional neural network. The subnetwork 105 according to one embodiment includes a CNN layer, with dropout for regularization and max pooling. Referring to FIG. 2, which illustrates implementation of a CNN architecture 200 according to an embodiment, an embodiment converts the irregularly timed claims and clinical data 102 into a sentence that is comprised of phrases that represent coded versions of medical events taking place in a patient's history. In natural language (input data is a sentence according to an embodiment), a filter is different than the one seen in image data. Words in input sentences are first embedded to dimension emb_dim. The width of the filters 201 is kept the same as emb_dim, but the height varies. In the illustrated example, emb_dim=5 and the sentence length is 7. Using filters 201 of sizes 4, 3, 2 with stride of 1, the illustrated embodiment respectively obtains feature maps 202 of sizes 4, 3, and 6. The strongest from each filter 201 is picked in the max-pooling operation 203, and results from all filter maps 202 are combined into a flattened layer to feed the autoencoders 111.

Recurrent neural network. The subnetwork 200 according to one embodiment feeds the training data 102 into a bidirectional LSTM following tanh activations, with hard sigmoid recurrent activations and glorot uniform kernel initialization. Optionally, an embodiment implements an attention layer at this step as well.

Figure 3:
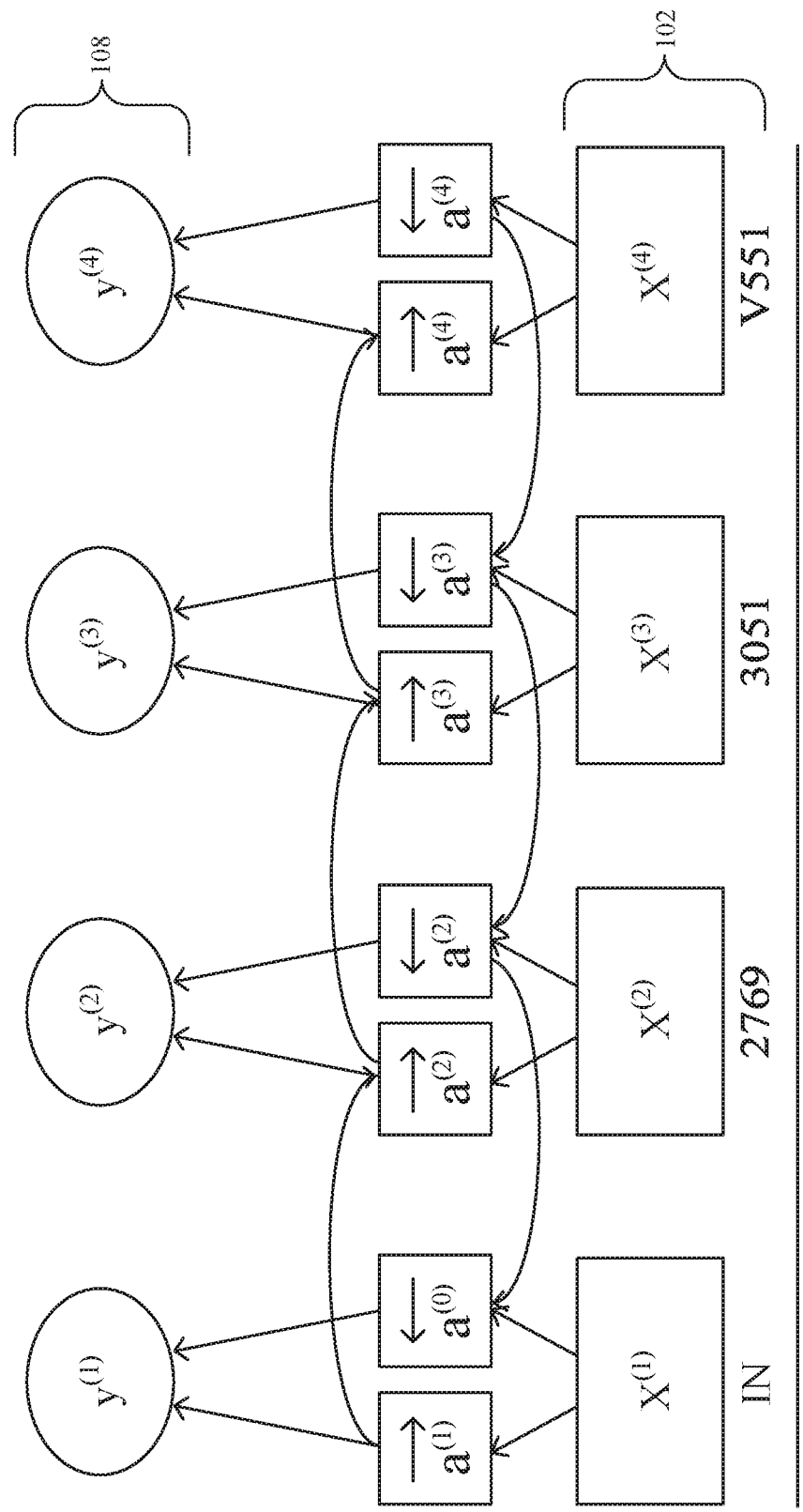
FIG. 3 is a schematic view of a long short-term memory unit of a recurrent neural network according to an embodiment of the invention.

FIG. 3 illustrates a bi-directional LSTM according to an embodiment on sample sentence "IN 2769 3051 V551" coded as X_1, X_2, X_3, X_4. Elements a_1, a_2, a_3, a_4 with an arrow pointing to the right in the illustration denote forward components of the network, which are LSTM units. Elements a_0, a_2, a_3, a_4 with an arrow pointing to the left in the illustration denote backward components of the network. Outputs 108 are denoted by y_1, y_2, y_3, y_4. Backward components learn by going backward in time. That is, while the forward components learn in the sequence a_1→a_2→a_3→a4, the backward components learn in the sequence a_4→a_3→a_2→a_0. The advantage of such a network is that in order to make predictions for y_3, for example, not only do inputs X_1, X_2, X_3 contribute but input from X_4 also makes its contribution with the help of a backward connection (i.e., pointing to the left in the illustration).

For neural subnetwork 106 processes data input one of three to produce a third output data set that can be output by a third primary output layer 109. This input stream may be highly dependent on the use case and the population under investigation, but generally it offers a novel method of processing time-series data collected from not-infrequent lab results. Whereas the Deepr paper ignores lab results, the Deep Patient paper simply counts the frequency of lab procedures, and the Scalable paper bins the numeric values roughly into tokens as an embodiment does. Here, an embodiment implements a subnetwork 106 that explicitly takes advantage of the structure of lab result time series.

From analyzing the use case and the population, an embodiment allows a user to draw up a list of lab procedures for which the user may expect sufficient data (e.g., most members in the population can have at least six reported results for these procedures). In an embodiment, there may be two options for processing this time-series data; in practice, a combination of both can be used.

Fit time series with analytic function. For each lab procedure, and as shown in FIG. 1, plot the lab results of a member, and fit it with an appropriate analytic function, as may be determined by a domain expert (e.g., linear, exponential, periodic). Extract coefficients from each fitting (e.g., slope and intercept), for each lab procedure. This option may require the lab results to be numeric values. The result is a sublayer of fixed size.

Recurrent neural network. Implement an RNN in a manner such as that described in Z. Che, S. Purushotham, K. Cho, D. Sontag, and Y. Liu, "Recurrent Neural Networks for Multivariate Time Series with Missing Values," *Sci. Rep.*, vol. 8, no. 1, p. 6085, April 2018 ("RNN paper"), which is hereby incorporated by reference as if fully set forth herein, where back-filling or forward-filling is used to fill in missing values. This option can be used with numeric or categorical (e.g., pregnancy) tests.

Each of the three subnetworks 104, 105, 106 includes a respective output layer 107, 108, 109 of fixed size, and an embodiment can concatenate these output layers. For example, if the dense layers from static data ends in a layer 107 of 10 nodes, and the CNN or RNN of claim data outputs a layer 108 of 100 nodes, and the normalized lab time-series data yields a layer 109 of 20 nodes, an embodiment concatenates these into an input layer 110 of 130 nodes. An embodiment then implements a stack 111 of two de-noising autoencoders that may include the input layer 110, an intermediate layer 112, and an output layer 113. And with, for example, noise rate of 5%, following the Deep Patient paper but using salt-and-pepper rather than masking noise. This approach results in a higher-level data representation that is robust in accounting for missing values as well as data corruption, and is use-case agnostic.

Figure 4:
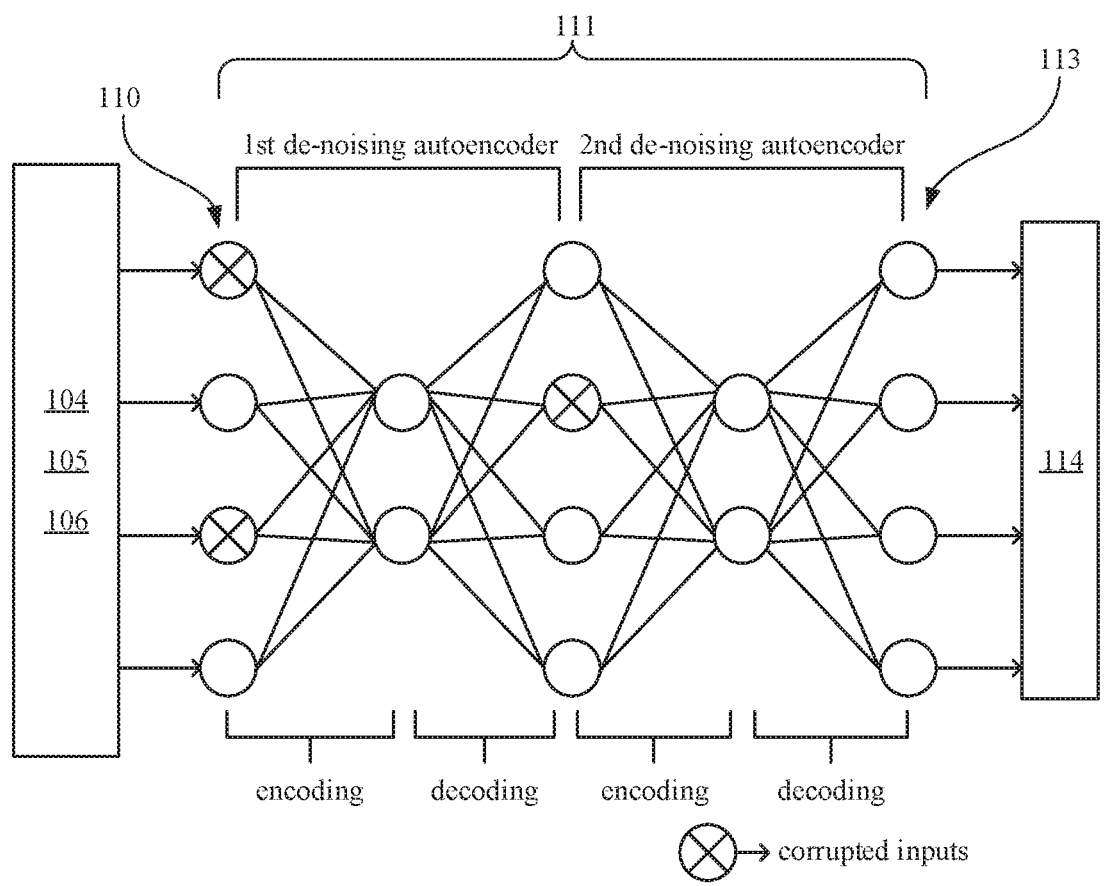
FIG. 4 is a schematic view of an autoencoder stack according to an embodiment of the invention.

FIG. 4 illustrates the autoencoder stack 111 according to an embodiment. Input from the subnetworks 104, 105, 106 are fed into a first denoising autoencoder. In the encoding region, salt-and-pepper noise is used, which randomly corrupts some of the inputs in the first layer. Neurons marked as 'X' signify corruption. During decoding, autoencoders learn robust representations of input data. These are fully connected networks. Two such autoencoders are stacked on top of each other where the output of the first becomes the input to the next. The final representation is sent from the output layer 113 to a classifier 114 for use-case specific classification needs.

Aggregating data from multiple data sources increases the number of potential features that phenomenologically influence, and hence enhance, the predictive power of the deep learning engine. Further, such aggregation of the data sources and news network subnets together makes prediction and learning about a much wider set of use cases feasible. For example, the set of healthcare use cases enabled by aggregating administrative (claims) and EHR data is much larger than what would be derived applying deep learning on either of the data sets alone. It follows that the insights gained from an aggregated DL architecture about individual records (such as patients, claims and encounters), and according to an embodiment, would be broader and more accurate than the alternative ML and deep learning methodologies available.

An embodiment allows a user to store, ingest, and train deep-learning networks on both structured data (e.g., lab, medication, and claim data) and unstructured data (e.g., call-center audio, clinical texts). Such data and data sources are described in G. M. Weber, K. D. Mandl, and I. S. Kohane, "Finding the Missing Link for Big Biomedical Data," *JAMA*, vol. 311, no. 24, pp. 2479-2480, June 2014, which is hereby incorporated by reference as if fully set forth herein. A key challenge in aggregating data sets is linking together a single patient's data among the variety of sources, and an embodiment includes a novel approach to linking records, which is detailed herein below.

Figure 5:
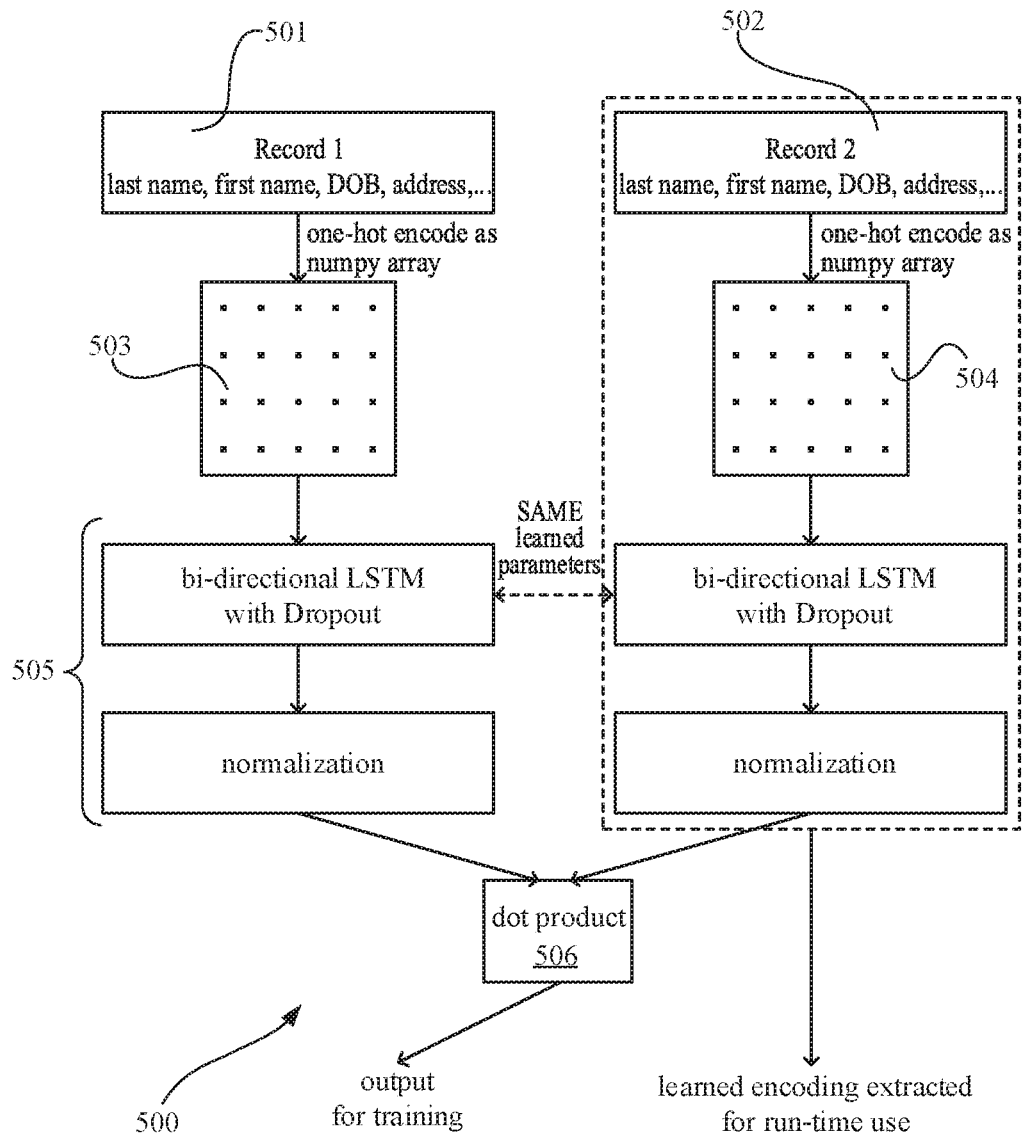
FIG. 5 is a schematic view of a record-linkage network according to an embodiment of the invention.

The record-linkage network 500, as illustrated in FIG. 5, is a form of Siamese network that includes a bidirectional LSTM recurrent neural network, and after normalization uses the dot product as the distance function. This is a variation on cosine distance that allows for improved runtime performance. By including L2-normalization in the encoding function, the runtime comparison of encoded pairs reduces to (very fast) matrix multiplication.

Each pair of data sources (e.g., reference database and US Census data, or reference database and clinical texts) has a small set of data attributes used for matching (e.g., last name, first name, date of birth, and/or address), and a different record linkage model is trained on each such pair of sources.

Consider one pair of data sources, for example a reference database and US Census data. To link a pair of records 501, 502, an embodiment first converts each record into a string, such as "LastName FirstName DateOfBirth Address", and one-hot encodes the characters into a numpy array 503, 504. Each array is passed to the same encoding subnetwork 505, which includes a bidirectional LSTM layer with Dropout, followed by L2-normalization. This pipeline, from original record to the normalized vector representation, may be referred to as the encoding function. Both records 501, 502 in the pair are passed through the same encoding function.

To learn the parameters of the encoding function, an embodiment combines them in a final layer 506 using the dot product, assigns a root-mean-square error (RMSE) loss function, and trains on a dataset of known matches (label 1) and non-matches (label 0). In this way, the model learns an encoding function such that, when two candidate records are compared using the dot product, they dot to one if a match and to zero if a non-match. This may be referred to as their match score.

To link varied and unstructured data to the unique patient IDs in the master data structure of an embodiment, such embodiment trains such an encoding function for each pair of data sources. The reference database can be encoded using the encoding functions, and stored for runtime matching.

When an unmatched record or batch of records comes in, these are fed through the corresponding encoding function and converted to their normalized vector representation. Then a simple matrix multiplication with the encoded reference database yields pair-by-pair match scores. (Matrix multiplication is the same as structured pair-by-pair dot products.) Matrix multiplication of numpy arrays is an extremely fast computation, and in practice the pre-processing encoding step takes less than 20 milliseconds per record.

Using the pair-by-pair match scores, an embodiment can assign matches and non-matches using two confidence thresholds. If appropriate, candidate pairs with match scores falling between the thresholds can be sent for manual review.

An embodiment includes a submodule for concept extraction and interpretation. There are multiple applications of such a submodule, including, but not limited to, the following:

Phenotyping of text narratives: In one known approach, domain experts are used to label hospital discharge summaries as indicating phenotypes such as advanced cancer, chronic pain, and obesity. An embodiment extends the source list to include free-text notes extracted from clinical note transcriptions, call center transcriptions, as well as social media. The list of phenotypes includes straightforward categories such as cancer, heart disease, and lung disease, as well as broader categories such as chronic pain, alcohol abuse, and depression.

The purpose of this application is to tag individual text comments with appropriate disease/concept flags, which can be used elsewhere in an embodiment. For example, by processing and tagging a clinical note attached to a professional claim, an embodiment can include those tokens with the claim in the patient's "sentence" in the model described above herein. This allows an embodiment to intelligently incorporate the substance of the clinical note without blowing out the dimension of the token space.

Patient phenotyping using claim and text data: An embodiment includes procedure and diagnosis codes, and prescription National Drug Code (NDC) codes. An embodiment includes lab procedures optionally advantageously by their Logical Observation Identifier Names and Codes (LOINC) code, not their result values. Furthermore, unlike in the larger model architecture according to an embodiment, an alternative embodiment removes the temporal element from these code tokens by gathering them together and randomizing their order. This is done in order to improve interpretability, as discussed below.

The purpose of this application is to tag individual patients (or individual claims, depending on the use case) with disease/concept flags, which can be used elsewhere in an embodiment. For example, it allows an embodiment to study the subpopulation flagged as "smoker" or "alcoholic". Or, by filtering for those flagged as "diabetic" prior to training the full model according to an embodiment described above herein, an embodiment can curate the lab procedures included in the time-series analysis subnetwork to those lab tests most relevant to diabetic patients.

Detection of risk, waste, and fraud: This application starts from a concept or concepts that are of interest from a healthcare perspective, such as waste or fraud. An embodiment assumes the labels are assigned externally certain patients or certain claims have been identified as wasteful or fraudulent. The input data sources are chosen appropriately as above: either just text data, or just codes, or the combination of the two. Again, an embodiment removes the temporal aspect for interpretability and to allow to train a sufficiently general classifier.

The purpose of this application is to understand the patterns of codes and text in a patient's records that are indicative of an important concept, such as risk, or waste, or fraud. After training to detect fraud, for example, this learned sub-model serves as a fraud filter, and its interpretation highlights the code/text patterns that suggest fraud.

Described below is a deep learning architecture used in this submodule according to an embodiment and how it is well-suited for interpretability.

In each of the above settings, text data is tokenized and connected to a learnable embedding layer, which is either randomly initialized or initialized with word2vec. Procedure, diagnosis, prescription, and lab codes are gathered and reordered randomly; since these codes cannot appear in the word2vec corpus, their embedding vectors are initialized randomly making sure that the variance matches the variance of embedded text data.

Embedding vectors are fed into a CNN layer, or several such layers, with appropriate regularization using dropout. The final layer includes softmax activation for multiclass classification.

In an interpretability submodule according to an embodiment, the input data is simplified by removing temporality, removing static demographic features, and simply counting lab procedure codes rather than their actual result values. This approach promotes interpretability and generality. One or more embodiments may employ the following methods for interpreting learned neural network models:

Maximum activation analysis—This technique finds training examples that result in maximum activation at specific neurons in the network.

Saliency analysis—This technique is described in S. Gehrmann et al., "Comparing deep learning and concept extraction based methods for patient phenotyping from clinical narratives," *PLOS ONE*, vol. 13, no. 2, p. e0192360, February 2018 and J. Li, X. Chen, E. Hovy, and D. Jurafsky, "Visualizing and Understanding Neural Models in NLP," *ArXiv*150601066 *Cs*, June 2015, which are hereby incorporated by reference as if fully set forth herein. This technique calculates the norm of the gradient of the loss function with respect to an input or combination of inputs. Roughly speaking, larger values correspond to inputs or input phrases that matter more to the output.

These interpretation analyses are done at the final classification layer, as well as the last hidden layer. In the former case, for example, an embodiment could learn what specific diagnosis or procedure codes, or words in a clinical text, correspond to labeling a patient as "depressed", or a claim as "fraudulent." In the latter case, an embodiment can extract distinct high-level characteristics of the label attribute, for example, the code patterns that reveal the distinct types of waste (e.g., unnecessary procedure, too-frequent doctor visits, avoidable ER visit).

An architecture according to an embodiment and described above herein allows for a natural incorporation of domain expertise and use-case customization. An embodiment can simply assign additional tokens to the training data, in two possible locations:

Patient-level: For a tag that applies to an individual patient (e.g., "smoker"), place the token at the start of their claim history sentence.

Claim-level: For a tag that applies to a specific claim (e.g., "rejected"), place the token at the start of the claim phrase (e.g., "PRF REJ 2769 3051 V551")

These additional tokens can, in an embodiment, be generated in two ways:

Automatically: Using the concept extraction methods described above. This is a form of transfer learning, where an embodiment uses code/text patterns learned elsewhere to enhance the quality of the data for a specific use case.

By hand: Domain experts generate a master list of potentially relevant attributes; using correlation methods such as PCA, similarity and interestingness; additional/alternative attributes can also be identified. Together, these attributes form a set of highly relevant features, which are used to flag records and assign additional tokens.

In this way, expert knowledge can be transferred and carried throughout the deep learning models, to customize for specific use cases and improve performance.

Time is a crucial factor in healthcare—diseases change their course over time and so do the health determinant factors of a patient. In the context of an embodiment, healthcare payer provider ecosystem can, in an embodiment, be modeled as a large hyperspace containing three types of objects—animate objects (e.g., doctors, patients, nurses, caregivers, administrators, etc.), inanimate objects (devices, hospitals, drugs, etc.) and abstract objects (claims, payments, procedures, etc.) Each such object is represented as a machine learning data frame with a structured data part and unstructured data part. Aggregation of such data representing many objects in the hyperspace is how the a master data set according to an embodiment is constructed. Interactions among animate objects such as doctors, patients and abstract objects such as claims, payments in time and space are thus the optionally advantageous deep learning representation of healthcare according to an embodiment of the present invention (Deep Claim). Further, each of the various payer provider business activities represents encounters among the objects described above. For example, a patient's visit (encounter) is an encounter of the following objects: doctor, patient, support staff, medical devices, claim, chart, prescription and payment. Many of the variables or attributes defining such encounter are time-dependent. Thus, tracking, modeling and analysis of healthcare data as a function of time is an optionally advantageous prerequisite for the effective use of an embodiment to model healthcare. An embodiment provides a novel approach to representation of time-series data and suggests some ways of using this representation that will make the complexity of understanding and usage of such data feasible and effective.

Healthcare industry today is not just interested in the present state of a patient but also her past and how her health is expected to change over time. As an example, a patient's blood pressure is time dependent. A change in a person's blood pressure could be triggered by another time-dependent factor like loss of a caregiver, loss of social support or change in other clinical measurements. By monitoring and studying this trend of blood pressure, an embodiment can not only understand the reasons behind the fluctuations but also if the change in blood pressure has resulted in change of medication adherence and other treatment quality metrics. This also allows an embodiment to make effective time-specific predictions. Another example is in the hospital readmission area where a patient's likelihood of readmission changes with time when changes in her measurements are observed.

An embodiment provides an a novel representation of time-series data:

Consider D, a structured data set x[i, t], y[i, t] such that all variables including the predicted variable y are varying with time t.

Each variable can be represented as a time series in t.

A tensor T can represent the snapshots of D in t. Two novel efforts are provided in an for healthcare and in general as well:

A hybrid ML algorithm(s) that reconciles classification of y at each t_j value AND y as a function oft (i.e., time series);

A hybrid DL algorithm(s) that does the same.

In an embodiment described above herein, the incorporation of time-series data from lab results was detailed, by fitting analytic functions to the data, extracting coefficients (e.g., slope and bias), and combining these into a densely connected layer.

One or more embodiments may also provide the following functionality for capturing time dependency in healthcare data, dependent on use case and data quality. Each could be incorporated into the architecture according to an embodiment as an auxiliary input subnetwork, joining with other inputs at the layer prior to the autoencoders:

Checking if a time dependent value appeared more than one time in the dataset and marking it as a Yes or No boolean variable.

A binary variable to indicate whether the curve is linear or not.

Other time series based indices such as autoregressive integrated moving average (ARIMA) to capture the optionally advantageous signature of time series.

In the case that the data representation x that is output by the final autoencoder level of an embodiment is being used to predict an output variable y (a healthcare-related variable that is expected to change with time), an embodiment can gather repeated representations, x_i, and predictions, y_i, from different time steps. Both x_i and y_i can be fed into an LSTM layer, which can either be fed as auxiliary input back into the architecture described above herein (thus reincorporating data from the prediction point), or used independently to predict future values of y.

An embodiment leverages current deep learning methodology (natural language processing, convolutional and recurrent neural nets, embeddings), combined with the most recent state-of-the-art developments (stacked de-noising autoencoders, attention) in a novel, integrated architecture especially designed for the healthcare industry applications, enhanced by at least five additional, novel capabilities. The resulting data representation is use-case agnostic and can be trained, applied, and transferred among use cases.

While the preferred embodiment of the invention has been illustrated and described, as noted above, many changes can be made without departing from the spirit and scope of the invention. Furthermore, the applications described in paragraphs [0082] to [0087] of the present utility application are only a small sample of the many applications of vital practical interest and value to the Healthcare Industry, such as automated correction of errors in healthcare claims, hospital readmissions prediction, opioids abuse prediction, healthcare quality metrics prediction and recommendation of interventions, patient satisfaction and engagement prediction etc. One or more embodiments of the invention presented here can similarly be used, and is intended to be used, to enhance the analytics required by many such applications to provide their services with more accuracy, better quality, time and cost efficiency. The invention has wide applicability to significantly improve healthcare analytics practice. Accordingly, the scope of the invention is not limited by the disclosure of the preferred embodiment. Instead, the invention should be determined entirely by reference to the claims that follow.

What is claimed is:

1. A system, comprising:
    first, second and third input data sets, the first input data set including demographic information characterizing a patient, the second and third input data sets characterizing a healthcare treatment history of the patient; and
    at least one processing device configured to implement a neural network, the neural network comprising:
    first, second and third neural subnetworks, the first neural subnetwork having a first primary output layer and being configured to process the first input data set to produce a first output data set, the second neural subnetwork having second primary output layer and being configured to process the second input data set to produce a second output data set, and the third neural subnetwork having a third primary output layer and being configured to process the third input data set to produce a third output data set, the first, second and third primary output layers configured to output the first, second and third output data sets, and
    an autoencoder layer coupled to the first, second and third neural subnetworks, the autoencoder layer having an input layer comprising the first, second and third output data sets received from the first, second and third primary output layers, the autoencoder layer configured to process the first, second and third output data sets to produce a secondary output data set.

2. The system of claim 1, wherein the second neural subnetwork comprises a recurrent neural network.

3. The system of claim 1, wherein the second neural subnetwork comprises a convolutional neural network.

4. The system of claim 1, wherein the autoencoder layer comprises a stack of multiple de-noising autoencoders.

5. The system of claim 1, wherein the second input data set characterizes randomly timed the administrations of health care to the patient.

6. The system of claim 1, wherein the third input data set comprises numerical measurements characterizing the health status of the patient.

7. At least one computer-readable medium on which are stored instructions that, when executed by one or more processors, enable the one or more processors to perform a method, the method comprising the steps of:
    receiving, with a neural network, first, second and third input data sets, the first input data set including demographic information characterizing a patient, the second and third input data sets characterizing a healthcare treatment history of the patient;
    processing the first input data set with a first subnetwork of the neural network to produce a first output data set, the first subnetwork having a first primary output layer;
    processing the second input data set with a second subnetwork of the neural network to produce a second output data set, the second subnetwork having a second primary output layer;
    processing the third input data set with a third subnetwork of the neural network to produce a third output data set, the third subnetwork having a third primary output layer, the first, second and third primary output layers configured to output the first, second and third output data sets to an autoencoder layer coupled to the first, second and third neural subnetworks; and processing, with the autoencoder layer, the first, second and third output data sets to produce a secondary output data set.

8. The method of claim 7, wherein the second subnetwork comprises a recurrent neural network.

9. The method of claim 7, wherein the second subnetwork comprises a convolutional neural network.

10. The method of claim 7, wherein the autoencoder layer comprises a stack of multiple de-noising autoencoders.

11. The method of claim 7, wherein the second input data set characterizes randomly timed the administrations of health care to the patient.

12. The system of claim 7, wherein the third input data set comprises numerical measurements characterizing the health status of the patient.

\* \* \* \* \*